(12) United States Patent
Tallman et al.

(10) Patent No.: US 9,250,188 B2
(45) Date of Patent: Feb. 2, 2016

(54) SYSTEM AND METHOD FOR MEASURING COOLING OF A COMPONENT

(71) Applicant: General Electric Company, Schenectady, NY (US)

(72) Inventors: James Albert Tallman, Scotia, NY (US); Peter Joel Meschter, Franklin, TN (US); Lawrence Bernard Kool, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 211 days.

(21) Appl. No.: 14/022,922

(22) Filed: Sep. 10, 2013

(65) Prior Publication Data

US 2015/0072432 A1    Mar. 12, 2015

(51) Int. Cl.
G01N 21/77    (2006.01)

(52) U.S. Cl.
CPC .................... *G01N 21/77* (2013.01)

(58) Field of Classification Search
CPC ..................................... G01N 21/77
USPC .......................... 436/2; 422/82.05
See application file for complete search history.

(56) References Cited

U.S. PATENT DOCUMENTS

| | | | |
|---|---|---|---|
| 4,259,431 A * | 3/1981 | Opitz et al. | 430/199 |
| 4,384,039 A * | 5/1983 | Opitz et al. | 430/422 |
| 6,234,755 B1 | 5/2001 | Bunker et al. | |
| 6,383,602 B1 | 5/2002 | Fric et al. | |
| 6,524,395 B1 | 2/2003 | Devine | |
| 7,334,993 B2 | 2/2008 | Sekihara et al. | |
| 7,388,204 B2 * | 6/2008 | Key et al. | 250/340 |
| 7,388,980 B2 | 6/2008 | Vaidyanathan | |
| 7,574,035 B2 | 8/2009 | Koonankeil | |
| 7,671,338 B2 * | 3/2010 | Key | 250/340 |
| 7,890,274 B2 | 2/2011 | Bunker et al. | |
| 8,208,711 B2 * | 6/2012 | Venkatachalam et al. | 382/141 |
| 8,768,646 B2 * | 7/2014 | Key | 702/136 |
| 2002/0177985 A1 * | 11/2002 | Kraft et al. | 703/7 |

(Continued)

FOREIGN PATENT DOCUMENTS

| | | |
|---|---|---|
| EP | 1739410 A1 | 1/2007 |
| JP | H03151501 A | 6/1991 |

OTHER PUBLICATIONS

Pedersen, D. R. et al, Journal of Heat Transfer 1977, 99, 620-627.*

(Continued)

*Primary Examiner* — Arlen Soderquist
(74) *Attorney, Agent, or Firm* — Ann M. Agosti

(57) ABSTRACT

A system and method for measuring cooling effectiveness of a component is disclosed. The method includes providing a component with a coating applied on a surface of the component. Further, the method includes supplying a first gaseous medium over a surface of the component through a plurality of holes in the component and feeding a second gaseous medium along the surface of the component. Further, the method includes exposing the surface of the component to the first and second gaseous mediums for a predetermined period. The method further includes obtaining an image of the surface of the component exposed to the first and second gaseous mediums for the predetermined period. The method includes analyzing the obtained image to determine whether at least a portion of the coating is removed from the surface of the component upon exposure to the second gaseous medium.

17 Claims, 3 Drawing Sheets

(56) References Cited

U.S. PATENT DOCUMENTS

| | | | |
|---|---|---|---|
| 2006/0291716 A1 | 12/2006 | Vaidyanathan et al. | |
| 2007/0290134 A1* | 12/2007 | Key et al. | 250/340 |
| 2008/0101683 A1* | 5/2008 | Zombo et al. | 382/141 |
| 2008/0237466 A1* | 10/2008 | Key | 250/330 |
| 2009/0066939 A1* | 3/2009 | Venkatachalam et al. | 356/237.1 |
| 2011/0119020 A1* | 5/2011 | Key | 702/135 |
| 2011/0164653 A1* | 7/2011 | Allen et al. | 374/43 |

OTHER PUBLICATIONS

Gladden, H. J. et al, NASA Technical Memoranhm 88931, 1987, 18 pages.*
Haring, M. et al, ASME paper 94-GT-171, 1994, 9 pages.*
Cofer, C. G. et al, Carbon 1995, 33, 389-395.*
Friedrichs, F. et al, ASME paper 95-GT-1, 11 pages.*
Buck, F. A. et al, ASME paper 95-GT-19, 10 pages.*
Chyu, M. K. et al, ASME paper 96-GT-430, 7 pages.*
Haslinger, W. et al, ASME paper 96-GT-436, 8 pages.*
Richter, J. et al, ASME paper 96-GT-463, 8 pages.*
Jung, K. et al, ASME paper 98-GT-64, 11 pages.*
Goldstein, R. J. et al, ASME paper 98-GT-174, 9 pages.*
Jacobseon, N. et al, Journal of the American Ceramic Society 1999, 82, 393-398.*
Cho, H. H. ASME paper 99-GT-38, 12 pages.*
Lampard, D. et al, Measuring Science and Technology 2000, 11, 933-941.*
Yang, Z. et al, Propulsion and Power Research 2012, 1, 36-47.*
Dring, R. P. et al, Journal of Engineering for Power 1980, 102, 81-87.*
Goldstein, R. J. et al, Journal of Heat Transfer 1982, 104, 715-711.*
Ammari, H. D. et al, Journal of Turbomachinery 1990, 112, 444-450.*
Chyu, M. K. et al, Journal of Turbomachinery 1999, 121, 257-263.*

* cited by examiner

SYSTEM AND METHOD FOR MEASURING COOLING OF A COMPONENT

BACKGROUND

The present disclosure relates generally to measuring cooling of a component and more particularly, to a system and method for measuring cooling effectiveness of a component.

A method of cooling an engine component includes providing an array of cooling holes on a surface of a component to enable formation of a cooling film that prevents overheating of the component during engine operation, for example. The effectiveness of an array of cooling holes in dispersing a cooling medium across the surface of a component is typically analyzed using known fluid computational methods. However, these methods have limitations in modeling the film cooling effectiveness accurately. Accurate fluid computational methods may require finite element grids on the surface of the component, which in turn requires long computation times and significant expenses to model temperature distribution on the film cooled surface.

A direct method of measuring cooling effectiveness of the component includes providing a thermocouple array on the surface of the component or pyrometer scanner to measure the surface temperature distribution. Such direct methods may require multiple thermocouples or a complex pyrometric system. Such measurement systems may not be capable of measuring the surface temperature distribution on the component at the desired resolution.

Thus, there is a need for an improved system and method for measuring effectiveness of cooling of a component.

BRIEF DESCRIPTION

In accordance with one exemplary embodiment, a method of measuring cooling effectiveness of a component is disclosed. The method includes providing the component with a coating on a surface of the component. Further, the method includes supplying a first gaseous medium through a plurality of holes in the component for forming a cooling film of the first gaseous medium on the surface. The method further includes feeding a second gaseous medium along the surface of the component. The method includes exposing the component to a flow of the first and second gaseous mediums for a predetermined period. The method further includes obtaining an image of the surface of the component exposed to the flow of the first and second gaseous mediums for the predetermined period. Further, the method includes analyzing the obtained image to determine whether at least a portion of the coating is removed from the surface of the component upon exposure to the first and second gaseous mediums for the predetermined period. The removed portion of the coating is indicative of an ineffectively film cooled region on the surface of the component and a retained portion of the coating is indicative of an effectively film cooled region on the surface of the component.

In accordance with another exemplary embodiment, a method for measuring cooling effectiveness is disclosed. The method includes providing a component with a coating on a surface of the component. Further, the method includes supplying a first gaseous medium through a plurality of holes in the component for a predetermined period so as to form a cooling film of the first gaseous medium on the surface. The method further includes feeding a second gaseous medium along the surface of the component for the predetermined period so as to remove at least a portion of the coating upon exposure to the second gaseous medium. Further, the method includes obtaining an image of the surface of the component exposed to the first and second gaseous mediums. The method further includes analyzing the obtained image, in which the removed portion of the coating is indicative of an ineffectively film cooled region on the surface of the component and a retained portion of the coating is indicative of an effectively film cooled region on the surface of the component.

In accordance with one exemplary embodiment, a system for measuring cooling effectiveness is disclosed. The system includes a first source for supplying a first gaseous medium through a plurality of holes in a component having a surface provided with a coating. Further, the system includes a second source for supplying a second gaseous medium along the surface of the component and an imaging device for obtaining an image of the surface of the component exposed to the first and second gaseous mediums for a predetermined period. The system further includes a processor-based device communicatively coupled to the imaging device to receive the image from the imaging device and analyze the obtained image. The analysis of the obtained image includes determining whether at least a portion of the coating is removed from the surface of the component upon exposure to the second gaseous medium. The removed portion of the coating is indicative of an ineffectively film cooled region on the surface of the component and a retained portion on the coating is indicative of an effectively film cooled region on the surface of the component.

DRAWINGS

These and other features and aspects of embodiments of the present disclosure will become better understood when the following detailed description is read with reference to the accompanying drawings in which like characters represent like parts throughout the drawings, wherein.

DETAILED DESCRIPTION

While only certain features of embodiments have been illustrated and described herein, many modifications and changes will occur to those skilled in the art. It is therefore to be understood that the appended claims are intended to cover all such modifications and changes as falling within the spirit of the invention.

Embodiments discussed herein disclose systems and associated methods for measuring effectiveness of cooling of a component. More particularly, certain embodiments disclose a system for measuring effectiveness of cooling of a surface of the component. The system in one example includes a coating device for applying a coating on the surface of the component, for instance, an airfoil. Further, the system includes a first source for supplying a first gaseous medium through a plurality of holes in the component. The system also includes a second source for supplying a second gaseous medium along the surface of the component. Further, the system includes an imaging device for obtaining an image of the surface of the component exposed to the first and second gaseous mediums. The system also includes a processor-based device communicatively coupled to the imaging device. The processor-based device is configured to obtain the image from the imaging device. The processor-based device is further configured to analyze the obtained image to determine whether at least a portion of the coating is removed from the surface of the component upon exposure to the second gaseous medium.

More specifically, certain embodiments disclose a method for measuring effectiveness of cooling of a component. More particularly, certain embodiments disclose a method for measuring effectiveness of cooling of a surface of the component. The method includes providing the component having a surface provided with a coating. Further, the method includes supplying a first gaseous medium through a plurality of holes in the component, for forming a cooling film of the first gaseous medium on the surface. Further, the method includes feeding a second gaseous medium along the surface of the component and exposing the component to a flow of the first and second gaseous mediums for a predetermined period. The method further includes obtaining an image of the surface of the component exposed to the first and second gaseous mediums, and then analyzing the obtained image to determine whether at least a portion of the coating is removed from the surface of the component upon exposure to the second gaseous medium. The removed portion of the coating is indicative of an ineffectively film cooled region on the surface of the component and a retained portion of the coating is indicative of an effectively film cooled region on the surface of the component.

Figure 1:
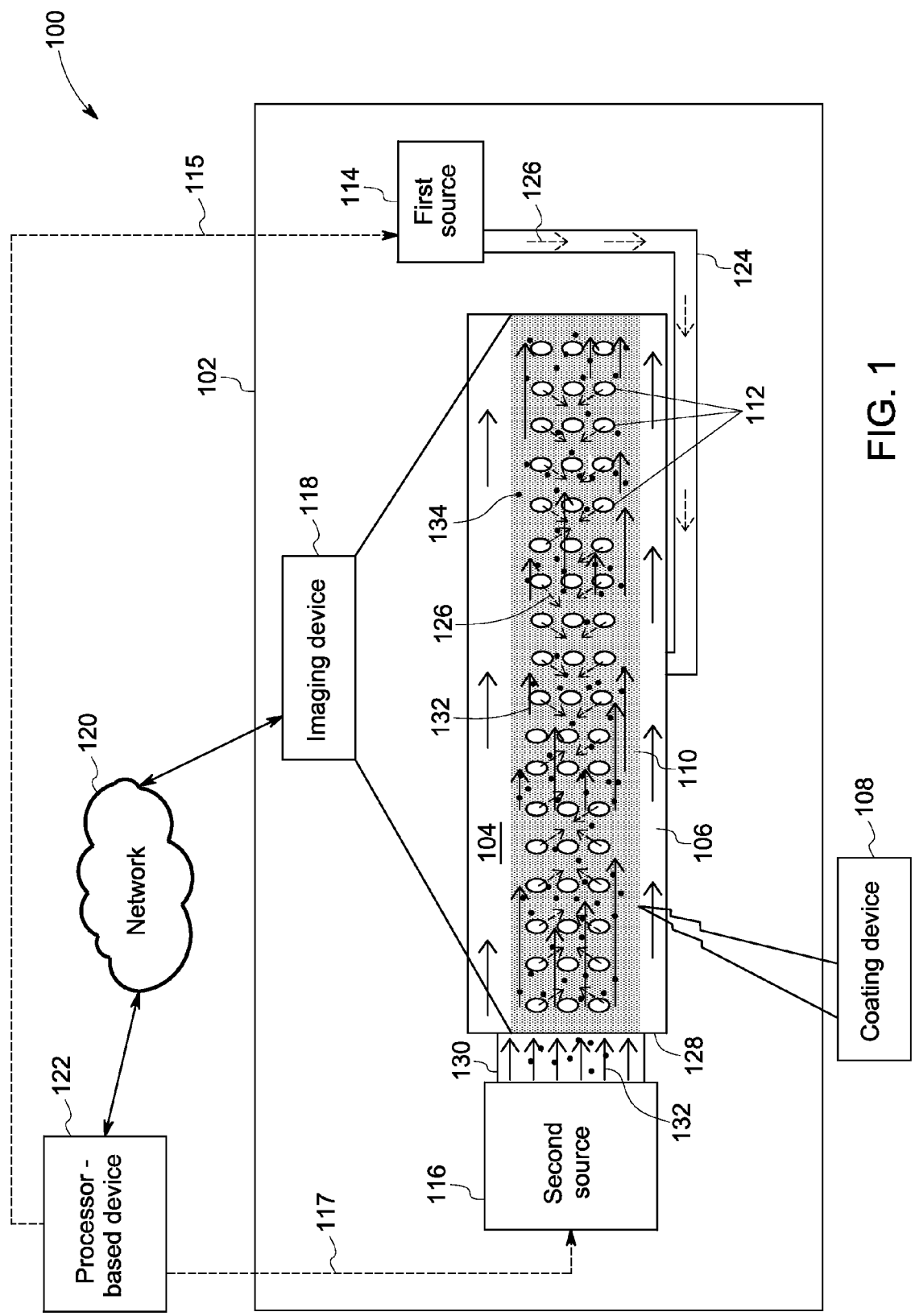
FIG. 1 is a schematic view of a system used for measuring cooling effectiveness of a component in accordance with one exemplary embodiment.

FIG. 1 is a schematic view of an exemplary system 100 for measuring cooling of a component 104. The system 100 includes a test device 102, a coating device 108, a first source 114, a second source 116, an imaging device 118, and a processor-based device 122.

In the exemplary embodiment, the test device 102 is a platform used for housing the component 104, the first source 114, and the second source 116. In the illustrated exemplary embodiment, additionally, the test device 102 also includes the imaging device 118. The coating device 108 is disposed external to the test device 102. In another exemplary embodiment, the imaging device 118 may be disposed external to the test device 102. Similarly, the coating device 108 may be housed within the test device 102. In one exemplary embodiment, the test device 102 may be a test rig. In another exemplary embodiment, the test device 102 may be a furnace test apparatus. In yet another embodiment, the test device 102 may be a turbine engine.

The component 104 may be part of a larger system, for example, a gas turbine engine, a jet engine, or the like. In one embodiment, the test device 102 may be deployed in a field environment for determining cooling effectiveness of an actual component. In some other embodiments, the test device 102 may be deployed in a lab environment or test environment for determining cooling effectiveness of a prototype component.

In the exemplary embodiment, the component 104 is disposed in the test device 102 for measuring the effectiveness of cooling of the component 104. The component 104, in one example, is an engine component. In certain embodiments, the component 104 may be a gas engine component, a turbine component, an airfoil, a test specimen, a prototype component, or the like. In some other embodiments, the component 104 may be a combustor liner, a blade (bucket), a vane (nozzle), a shroud, or the like. The component 104 includes a coating 110 disposed on a surface 106 of the component 104.

It should be noted herein that the coating 110 may be applied by suitable methods such as plasma spraying, aerosol spraying, painting, dipping, or the like.

In the exemplary embodiment, the component 104 includes a plurality of holes 112, for example, through-holes for feeding a first gaseous medium 126 such as air, for example. In one example, each hole among the plurality of holes 112 has a diameter in the range of one to two millimeters. The plurality of holes 112 may be cooling holes, leakage holes, or backside airflow holes. The location and the dimension of the plurality of holes 112 may vary depending on the application and design criteria. The plurality of holes 112 may be formed using suitable techniques such as drilling, milling and the like. When the first gaseous medium 126 is fed through the plurality of holes 112, a cooling film (not shown in FIG. 1) is formed on the surface 106 of the component 104, to prevent overheating of the component 104 and hence prevent loss of mechanical properties of the component 104. Additionally, in the exemplary embodiment, the surface 106 of the component 104 is exposed to a flow of a second gaseous medium 132, such as a combustion gas, for example.

The second gaseous medium 132 includes a reactant 134 and the first gaseous medium 126 does not include the reactant 134. In the exemplary embodiment, the reactant 134 includes at least one of oxygen, carbon dioxide, water vapor, and a species of gaseous halide. The species of gaseous halide may include fluorine, chlorine, bromine, and iodine. The second gaseous medium 132 may include water vapor in the range of 1 percent to 100 percent by volume. In one specific embodiment, the second gaseous medium 132 may include water vapor in the range of 5 percent to 20 percent by volume. It should be noted herein that the coating 110 is volatilized if there is presence of the reactant 134 in the second gaseous medium 132. The coating 110 is not volatilized if there is presence of the cooling film of the first gaseous medium 126. The reactant 134 is introduced to volatilize a portion (not shown in FIG. 1) of the coating 110 which is not effectively covered by the flow of the first gaseous medium 126.

The coating 110 may be applied on at least a portion of the surface 106. In one embodiment, the surface 106 may be an inner surface of the component 104 that is exposed to the flow of the first and second gaseous mediums 126, 132 respectively. In some other embodiments, the surface may be an outer surface of the component 104. It should be noted herein that the exemplary coating 110 may be applicable to any suitable surface and any suitable component exposed to the flow of the first and second gaseous mediums 126, 132. The coating 104 may include inorganic compounds comprising at least one of an oxide, carbide, a nitride of at least one of boron, chromium, silicon, nickel, cobalt, iron, and the like.

In the exemplary embodiment, the coating device 108 is used to apply the coating 110 on the surface 106 of the component 104. The coating device 108 may be a plasma sprayer or an aerosol sprayer or a painting device or the like. In the exemplary embodiment, the coating 110 may be applied on the surface 106 by at least one of plasma spraying, aerosol spraying, dipping, and painting. In the exemplary embodiment, the first source 114 is coupled to the component 104 via a transfer line 124. The first source 114 is used to feed the first gaseous medium 126 to the component 104 via the transfer line 124. Specifically, the first gaseous medium 126 is fed to the surface 106 of the component 104 through the plurality of holes 112. The first gaseous medium 126 forms the cooling film on the surface 106 of the component 104. The first gaseous medium 126 may be a dry medium including at least one of air, argon, nitrogen, or the like. It should be noted herein that the dry medium does not volatilize a retained portion (not shown in FIG. 1) of coating 110 which is covered by the flow of the first gaseous medium 126. In some embodiments, the first source 114 may have a valve (not shown in FIG. 1) for controlling a flow of the first gaseous medium 126 fed to the component 104.

In the exemplary embodiment, the second source 116 feeds the second gaseous medium 132 to the surface 106 of the component 104 via a feed line 130. The second gaseous medium 132 may be a combustion gas generated by burning a fuel such as natural gas, liquid jet fuel, liquid diesel fuel, or the like. In the illustrated embodiment, the reactant 134 in the second gaseous medium 132, is water vapor capable of volatilizing the portion of the coating 110 to which the second gaseous medium 132 is contacted. In certain other embodiments, the second gaseous medium 132 may include other reactants capable of volatilizing the portion of the coating 110 to which the second gaseous medium 132 is contacted. In one example, the second gaseous medium 132 may be in the temperature range of about 650-2200 degrees Fahrenheit. In one specific example, the second gaseous medium 132 may be in the temperature range of about 650-800 degrees Fahrenheit. In some embodiments, the second source 116 may have a valve (not shown in FIG. 1) for controlling the flow of the second gaseous medium 132 over the component 104.

In an exemplary embodiment, the imaging device 118 is configured to obtain one or more images of the component 104. Specifically, the imaging device 118 is configured to obtain images of the surface 106 of the component 104 exposed to the first and second gaseous mediums 126, 132. The imaging device 118 may be a photography device, an infrared imaging device, or the like. The imaging device 118 may capture image of the surface 106 of the component 104 by photography, a reflectivity measurement, profilimetry, or the like. Further, the imaging device 118 is communicatively coupled to the processor-based device 122 via a network 120. It should be noted herein that the configuration of the system 100 may vary depending on the application and design criteria.

The processor-based device 122 is further communicatively coupled to the first source 114 via a first communication link 115. The processor-based device 122 controls the first source 114 for controlling a flow rate and duration of flow of the first gaseous medium 126 from the first source 114. The duration of flow of the first gaseous medium 126 may be for a predetermined period, for example, around ten minutes. Further, the processor-based device 122 is communicatively coupled to the second source 116 via a second communication link 117. The processor-based device 122 controls the second source 116 for controlling a flow rate and duration of flow of the second gaseous medium 132 from the second source 116. The duration of flow of the second gaseous medium 132 may be for a predetermined period, for example, around thirty minutes. In such embodiments, an optimal flow rate and duration of the first gaseous medium 126 and the second gaseous medium 132 is maintained to accurately determine the cooling effectiveness of the component 104.

In the exemplary embodiment, the processor-based device 122 is configured to obtain the image of the component 104. Specifically, the processor-based device 122 is configured to analyze the obtained image to determine whether at least a portion of the coating 110 is removed from the surface 106 of the component 104 upon exposure to the first and second gaseous mediums 126, 132 for the predetermined period. The processor-based device 122 is further configured to determine an ineffectively film cooled region i.e. a non-cooled region and an effectively film cooled region i.e. a cooled region on the surface 106 of the component 104.

A removed portion of the coating 110 is indicative of an ineffectively film cooled region on the surface 106 and the retained portion of the coating 110 is indicative of an effectively film cooled region on the surface 106. Determination of the effectively film cooled region and ineffectively film cooled region on the surface 106 facilitates a measurement of the cooling effectiveness of the component 104.

Figure 2:
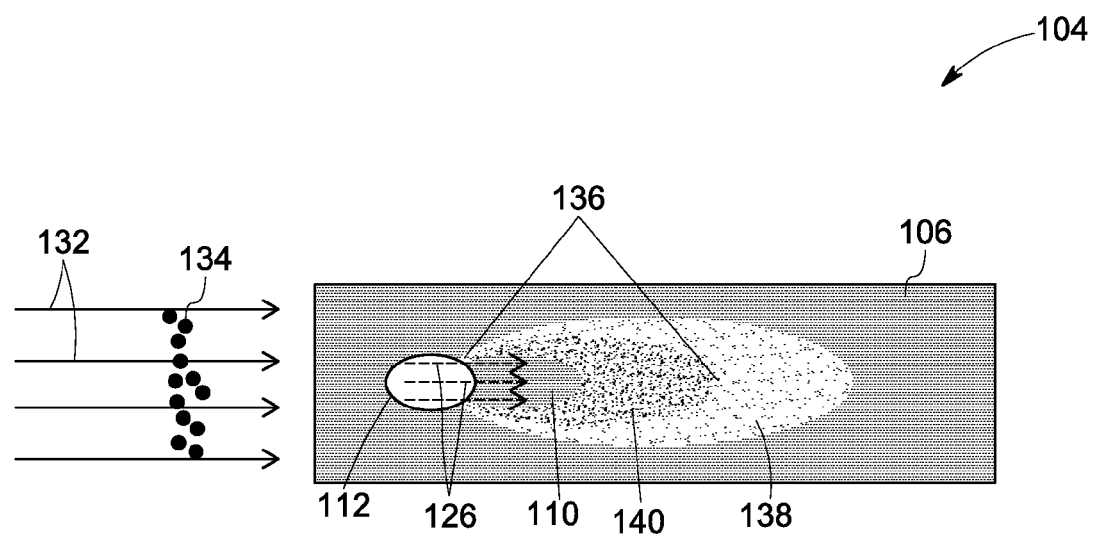
FIG. 2 is a schematic view of a surface of a component exposed to a first gaseous medium and a second gaseous medium in accordance with one exemplary embodiment.

FIG. 2 is a schematic representation of the surface 106 of the component 104 exposed to the second gaseous medium 132 and the first gaseous medium 126, in accordance with one exemplary embodiment. The component 104 includes the coating 110 disposed on the surface 106 and the plurality of holes 112. The first gaseous medium 126 is fed onto the surface 106 of the component 104 through the plurality of holes 112. The first gaseous medium 126 forms a cooling film 136 over the surface 106 so as to provide cooling to the component 104. Similarly, the second gaseous medium 132 having the reactant 134, for example, water vapor is fed along the surface 106 of the component 104. The component 104 is exposed to a flow of the first and second gaseous mediums 126, 132. The flow of the second gaseous medium 132 along the surface 106 of the component 104 results in reaction of the water vapor 134 with at least a portion of the coating 110 not covered by the cooling film 136 to form a gaseous reaction product. The reaction results in volatilization of at least a corresponding portion of the coating 110. The volatilization results in formation of a removed portion 138 of the coating 110 on the surface 106 of the component 104. The removed portion 138 of the coating 110 is indicative of an ineffectively film cooled region on the surface 106 of the component 104. A retained portion 140 of the coating 110 is indicative of an effectively film cooled region on the surface 106 of the component 104.

In one exemplary embodiment, the second gaseous medium 132 includes water vapor that is capable of volatilizing the portion of the coating 110 that is not covered by the cooling film 136, upon exposure to the second gaseous medium 132. In some other embodiments, the second gaseous medium 132 includes oxygen or carbon-dioxide that is capable of reacting with the portion of the coating 110 that is not covered by the cooling film 136, upon exposure to the second gaseous medium 132 to form the removed portion 138 of the coating 110. The retained portion of the coating 140 that is covered by the cooling film 136 is not volatilized.

Figure 3:
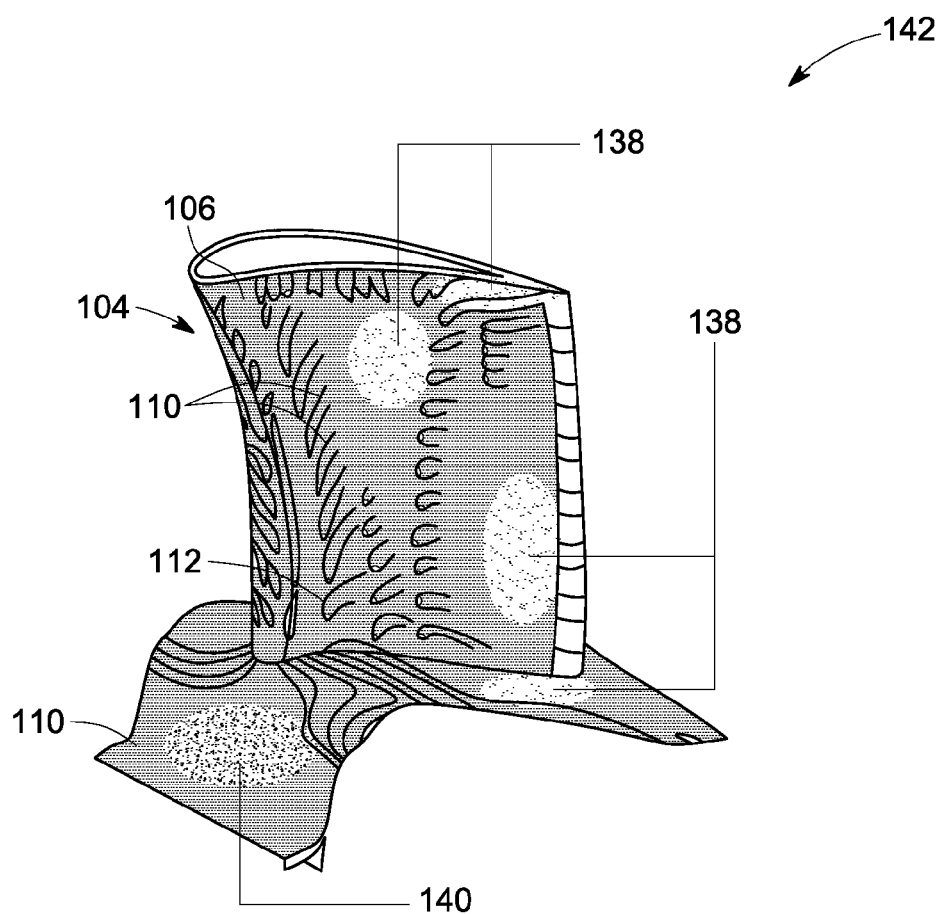
FIG. 3 is a perspective view of an image of a component in accordance with one exemplary embodiment.

FIG. 3 is perspective view of an image 142 of the component 104 in accordance with one exemplary embodiment. The image 142 may be a photographic image, a rastered image of surface roughness obtained by profilimetry, or an image of remnant coating thickness obtained by a suitable nondestructive evaluation technique such as infrared thermography. The component 104 includes the plurality of holes 112 and the coating 110 applied over the surface 106. The removed portion 138 of the coating 110 that is not covered by the cooling film 136 (as shown in FIG. 2), is indicative of an ineffectively film cooled region on the surface 106 of the component 104. The retained portion 140 of the coating 110 that is covered by the film cooling 136 (as shown in FIG. 2) is indicative of an effectively film cooled region on the surface 106 of the component 104.

Figure 4:
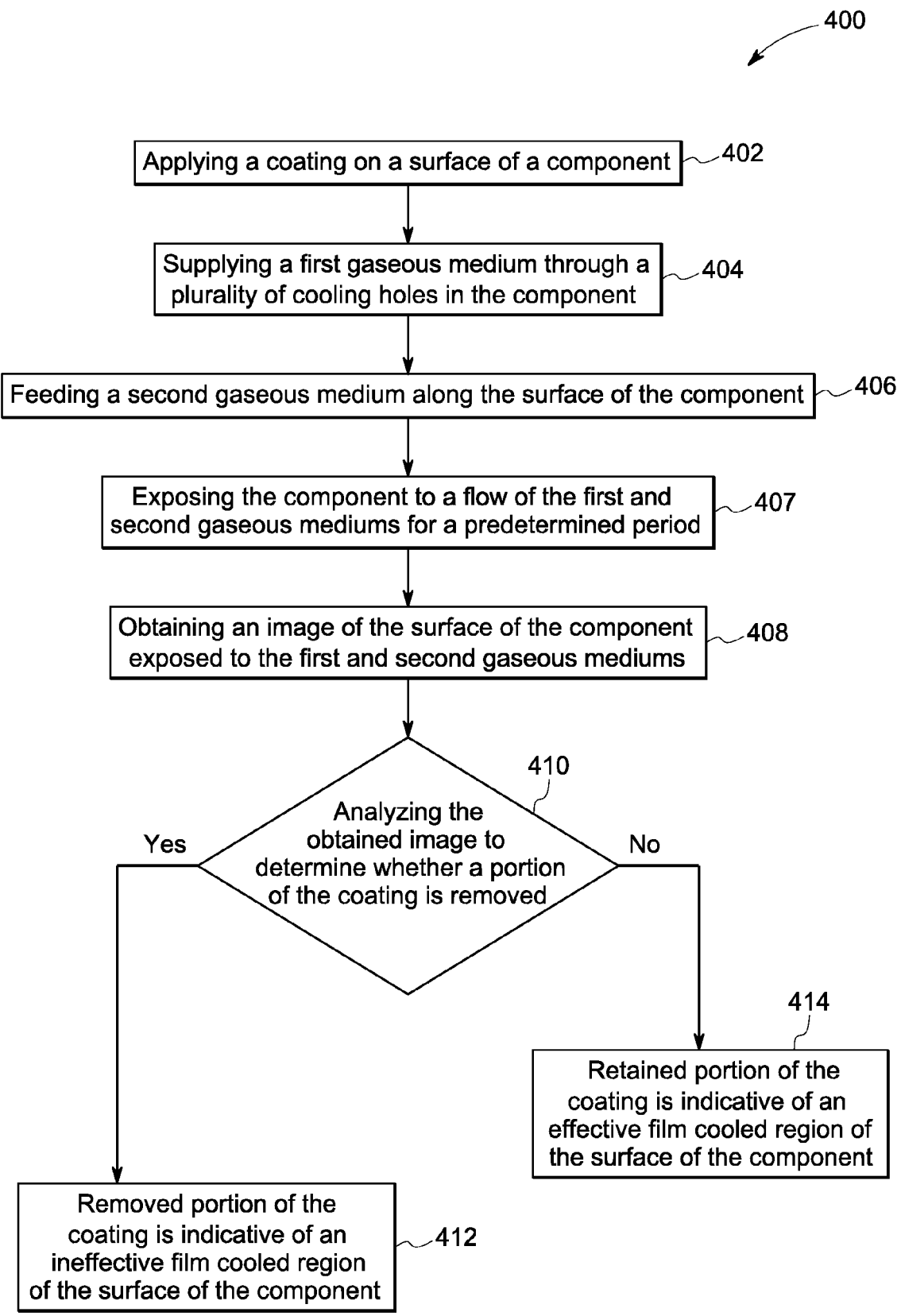
FIG. 4 is a flow chart illustrating steps involved in measuring cooling effectiveness of a component in accordance with one exemplary embodiment.

FIG. 4 is a flow chart illustrating an exemplary method 400 for measuring cooling effectiveness of a component in accordance with an exemplary embodiment.

The method 400 includes applying a coating on a surface of a component 402 in accordance with one exemplary embodiment. The coating may include an inorganic compound comprising at least one of an oxide, carbide, and nitride of at least one chemical element, such as boron, chromium, silicon, nickel, cobalt, iron, or the like. A first gaseous medium is fed through a plurality of cooling holes in the component 404. Specifically, the first gaseous medium being a dry medium, for example, is supplied to the surface of the component so as to form a cooling film on the surface of the component. Such a cooling film provides cooling to the surface of the component so as to prevent overheating of the component. The first gaseous medium may be air, nitrogen, argon, or the like.

A second gaseous medium is fed along the surface of the component 406. The surface of the component is exposed to a flow of the first and second gaseous mediums 407 for a predetermined period. The component may be exposed to a surface temperature in a range of 650-2200 degrees Fahrenheit. The second gaseous medium may include a reactant such as water vapor, for example. It should be noted herein that the component is not adequately cooled in regions where the coating is not adequately covered by the cooling film of the first gaseous medium. In the exemplary embodiment, one or more inorganic compounds of the coating are sensitive to the reactant of the second gaseous medium. Such inorganic compounds are readily volatilized upon exposure to the second gaseous medium comprising the reactant, such as water vapor, to form a gaseous reaction product. The flow of the second gaseous medium along the region of the coating that is not adequately covered by the cooling film results in volatilization of the coating. The volatilization of the coating occurs due to the reaction of water vapor in the second gaseous medium with at least one inorganic compound of the coating, resulting in removal of a corresponding portion of the coating from the surface of the component. Similarly, the flow of the second gaseous medium along a region of the coating that is adequately covered by the cooling film does not result in volatilization of the coating. In one exemplary embodiment, the second gaseous medium and the first gaseous medium are supplied for a predetermined duration and at a predetermined flow rate. The supply of the first gaseous medium and the second gaseous medium above the predetermined flow rate and the duration may result in full removal of the coating. Similarly, the supply of the first gaseous medium and the second gaseous medium below the predetermined flow rate and the duration may result in partial removal of the coating. In one such embodiment, the predetermined duration may in the range of about five to ten minutes and the predetermined flow rate may in the range of about five cubic meters per second to eight cubic meters per second.

An image of the surface of the component exposed to the second gaseous medium is obtained 408. The obtained image is analyzed to determine whether at least a portion of the coating is removed from the surface of the component 410. In one embodiment, differences in contrast between the regions (i.e. cooled region and non-cooled region) may be an indicator to determine the cooling effectiveness of the component. In the illustrated embodiment of FIG. 3, the region where the coating is retained has a lighter shade and is indicative of an effectively film cooled region on the component. The region where the coating is removed has a darker shade and is indicative of an ineffectively film cooled region on the component. A removed portion of the coating is indicative of an ineffectively film cooled region i.e. a non-cooled region on the surface of the component 412. The non-cooled region is also indicative of the region of the coating that is not adequately covered by the cooling film. The retained portion of the coating is indicative of an effectively film, cooled region i.e. a cooled region on the surface of the component 414. The cooled region is also indicative of the region of the coating that is adequately covered by the cooling film.

In one example, a boron nitride (herein also referred as "BN") coating is formed on a surface of an engine component. The component is then placed in a test rig and nitrogen is fed over the surface of the component via the plurality of holes in the component so as to form a nitrogen film over the surface of the component. Further, the component is subjected to a flow of a combustion gas comprising water vapor, at a temperature of 650-750 degrees Fahrenheit. The component may be exposed to the flow of the combustion gas and nitrogen for a predetermined period of fifteen minutes and at a temperature of 700 degrees Fahrenheit. A portion of the BN coating which is not covered by the nitrogen film, is removed because the water vapor in the combustion gas reacts with the BN coating to produce volatile products such as boric acid ("$B(OH)_3(g)$") and metaboric acid ("$(HBO_2)_3(g)$"). The retained portion of the coating is not removed since such a portion is covered by the nitrogen film. Thereafter, an image of the component exposed to the flow of nitrogen and combustion gas is obtained. The image is analyzed to determine the ineffectively film cooled regions and effectively film cooled regions on the engine component so as to measure the effectiveness of the cooling holes in the component.

Embodiments of the present invention discussed herein facilitate easily and economically determining the effectiveness of cooling holes disposed on the surface of the component, in a relatively low temperature test rig or under engine operating conditions. Further, the embodiments facilitate accurate design of such holes, as the techniques are based on the identified surfaces of the component which are subjected to volatilization of the coating.

The invention claimed is:

1. A method for measuring cooling effectiveness of a component, the method comprising:
   providing the component having a surface provided with a coating comprising an inorganic compound;
   supplying a first gaseous medium from a first source, through a plurality of holes in the component, for forming a cooling film of the first gaseous medium on the surface;
   feeding a second gaseous medium comprising a reactant, from a second source, along the surface of the component;
   exposing the component to a flow of the first and second gaseous mediums for a predetermined period, wherein the reactant chemically reacts with at least a portion of the coating to form a gaseous reaction product resulting in removal of the portion of the coating;
   obtaining at least one image via an imaging device of the surface of the component exposed to the flow of the first and second gaseous mediums; and
   analyzing the obtained image to determine whether at least the portion of the coating is removed from the surface of the component upon exposure to the first and second gaseous mediums for the predetermined period, wherein the removed portion of the coating is indicative of an ineffectively film cooled region on the surface of the component and a retained portion of the coating is indicative of an effectively film cooled region on the surface of the component.

2. The method of claim 1, wherein the inorganic compound comprises at least one of an oxide, carbide, and nitride of at least one of boron, chromium, silicon, nickel, cobalt, and iron.

3. The method of claim 1, further comprising applying the coating on the surface of the component by at least one of plasma spraying, aerosol spraying, dipping, and painting.

4. The method of claim 1, wherein the component comprises an engine component.

5. The method of claim 1, wherein the first gaseous medium is a dry medium comprising at least one of air, nitrogen, and argon.

6. The method of claim 1, wherein the second gaseous medium is a combustion gas, wherein the first gaseous medium does not contain the reactant.

7. The method of claim 1, wherein the reactant is at least one of oxygen, carbon dioxide, water vapor, and a species of gaseous halide.

8. The method of claim 6, wherein the second gaseous medium comprises water vapor in the range of 1 percent to 100 percent by volume.

9. The method of claim 1, wherein the exposing comprises maintaining a surface temperature of the component in a range of 650 to 2200 degrees Fahrenheit.

10. The method of claim 1, further comprising controlling the first source to control a flow rate and duration of flow of the first gaseous medium from the first source.

11. The method of claim 1, further comprising controlling the second source to control a flow rate and duration of flow of the second gaseous medium from the second source.

12. A method for measuring cooling effectiveness, the method comprising:
   providing a component having a surface provided with a coating comprising inorganic compound;
   supplying a first gaseous medium from a first source, through a plurality of holes in the component for a predetermined period, for forming a cooling film of the first gaseous medium on the surface;
   feeding a second gaseous medium comprising a reactant, from a second source, along the surface of the component for the predetermined period and removing at least a portion of the coating upon exposure to the reactant in the second gaseous medium by chemically reacting the reactant with the inorganic compound of the coating to form a removed portion of the coating;
   obtaining an image via an imaging device of the surface of the component exposed to the first and second gaseous mediums for the predetermined period; and
   analyzing the obtained image for the removed portion that is indicative of an ineffectively film cooled region on the surface of the component and for a retained portion of the coating that is indicative of an effectively film cooled region on the surface of the component.

13. A system and component combination comprising:
   a first fluid source coupled to the component for supplying a first gaseous medium through a plurality of holes in the component, said component having a surface provided with a coating comprising an inorganic compound;
   a second fluid source for supplying a second gaseous medium comprising a reactant, along the surface of the component;
   an imaging device for obtaining at least one image of the surface of the component exposed to the first and second gaseous mediums for a predetermined period, wherein the reactant chemically reacts with at least a portion of the coating to form a gaseous reaction product resulting in removal of the portion of the coating; and
   a processor-based device communicatively coupled to the imaging device, wherein the processor-based device is configured to:
      receive the image from the imaging device; and
      analyze the obtained image to determine whether at least a portion of the coating that is removed from the surface of the component upon exposure to the second gaseous medium, wherein the removed portion of the coating is indicative of an ineffectively film cooled region on the surface of the component and a retained portion of the coating is indicative of an effectively film cooled region on the surface of the component.

14. The system of claim 13, wherein the system comprises a test device for housing the component, the first source, the second source, and the imaging device.

15. The system of claim 13, further comprising a coating device for providing the coating on the surface of the component by at least one of plasma spraying, aerosol spraying, dipping, and painting.

16. The system of claim 13, wherein the processor-based device is further communicatively coupled to the first source and configured to control the first source for controlling a flow rate and duration of flow of the first gaseous medium from the first source.

17. The system of claim 13, wherein the processor-based device is further communicatively coupled to the second source and configured to control the second source for controlling a flow rate and duration of flow of the second gaseous medium from the second source.

* * * * *

UNITED STATES PATENT AND TRADEMARK OFFICE
CERTIFICATE OF CORRECTION

PATENT NO. : 9,250,188 B2
APPLICATION NO. : 14/022922
DATED : February 2, 2016
INVENTOR(S) : Tallman et al.

Page 1 of 1

It is certified that error appears in the above-identified patent and that said Letters Patent is hereby corrected as shown below:

In the specification,

In Column 4, Line 48, delete "coating 104" and insert -- coating 110 --, therefor.

In Column 6, Line 43, delete "coating 140" and insert -- coating 110 --, therefor.

In the claims,

In Column 9, Line 25, in Claim 12, delete "comprising" and insert -- comprising an --, therefor.

Signed and Sealed this
Fifth Day of July, 2016

Michelle K. Lee
*Director of the United States Patent and Trademark Office*